United States Patent [19]

Hatanaka

[11] Patent Number: 5,702,605

[45] Date of Patent: Dec. 30, 1997

[54] SLIME HYDROLASE PRODUCING BACTERIUM AND PROCESS FOR PRODUCING SLIME HYDROLASE

[75] Inventor: Katsuyuki Hatanaka, Kyoto, Japan

[73] Assignee: Sanyo Chemical Industries, Ltd., Kyoto, Japan

[21] Appl. No.: 776,396

[22] PCT Filed: Jul. 31, 1995

[86] PCT No.: PCT/JP95/01513

§ 371 Date: Jan. 28, 1997

§ 102(e) Date: Jan. 28, 1997

[87] PCT Pub. No.: WO96/04370

PCT Pub. Date: Feb. 15, 1996

[30] Foreign Application Priority Data

Aug. 1, 1994 [JP] Japan ................. 6-200083

[51] Int. Cl.⁶ ................. C12N 9/24; C02F 1/50; D21F 1/66
[52] U.S. Cl. ................. 210/632; 210/764; 162/161; 422/28; 435/183; 435/252.1; 435/264; 435/267; 435/822
[58] Field of Search ................. 210/606, 611, 210/632, 764; 162/161; 435/183, 252.1, 262.5, 264, 267, 281, 822; 422/28

[56] References Cited

U.S. PATENT DOCUMENTS

| | | | |
|---|---|---|---|
| 4,169,762 | 10/1979 | Hitzman | 435/243 |
| 4,941,533 | 7/1990 | Buller et al. | 166/270 |
| 5,212,079 | 5/1993 | Fujio et al. | 435/194 |
| 5,545,801 | 8/1996 | Fulton | 210/195.1 |

FOREIGN PATENT DOCUMENTS

| | | | |
|---|---|---|---|
| 0 388 115 A1 | 9/1990 | European Pat. Off. | C02F 1/50 |
| 4-91288 | 3/1992 | Japan | D21F 1/66 |
| 6-246257 | 9/1994 | Japan . | |

*Primary Examiner*—Thomas G. Wyse
*Attorney, Agent, or Firm*—Pollock, Vande Sande & Priddy

[57] ABSTRACT

A novel bacterium that can produce an enzyme having a wide specificity and being capable of decomposing slimes originating in various molds, yeasts and the like, more particularly, a novel bacterium of the genus Cellulomonas. The enzyme solution prepared by using the above bacterium is excellent in the effects of decomposition and prevention of formation of mold slime and can be applied for controlling slimes in industrial water, such as white water in the papermaking industry or cooling water, removing slime from separative membranes, preventing sludge bulking, washing garbage cages in a kitchen sink, and preserving wood.

17 Claims, No Drawings

SLIME HYDROLASE PRODUCING BACTERIUM AND PROCESS FOR PRODUCING SLIME HYDROLASE

TECHNICAL FIELD

The present invention relates to a slime-decomposing enzyme producing strain of microorganism which is capable of producing an enzyme useful for decomposing slime and a process for producing said slime-decomposing enzyme.

BACKGROUND TECHNOLOGY

A slime is a viscous mud-like substance composed predominantly of cellular components of microorganisms and products of their metabolism either suspended in a body of utility water or deposited on the wall surfaces of water lines and tanks. In particular, a slime is formed in paper-mill white water, gets deposited, grow, and as it attains a certain size, becomes exfoliated to cause various troubles in the paper-making industry.

It is known that not only bacteria but also Eumycetes inclusive of molds and yeasts exist in white water. Particularly in recent years, eutrophication of white water due to recycling of white water, an increased proportion of used paper in paper stock, and addition of starch, etc. has generated the problem of mold slime.

For control of formation of slimes, a variety of antimicrobial agents have heretofore been employed. Among them, organic nitrogen compounds, organosulfur compounds, organic nitrogen- and sulfur-containing compounds, and organobromine compounds are known.

With regard to microbicides and antimicrobial agents for slime control, the use of safety agents benign to the environment has been required. However, the appearance of resistant strains as well as pollution problems remain to be solved as yet.

As a class of biological preparations for slime control, various enzymatic agents are also known. For example, Japanese Kokoku Publication Sho-53-39395 (U.S. Pat. No. 3,773,623) discloses the use of levan hydrolase for decomposing levan, a product of metabolism in slime-forming microorganisms, for slime control. Being a kind of polysaccharide produced by bacteria, levan is a β-fructan with a backbone chain composed of β-2,6-fructofuranose residues.

Japanese Kokai Publication Sho-59-225103 (U.S. Pat. No. 4,684,469) discloses a binary composition comprising a biocidal substance and a polysaccharide-decomposing enzyme which includes levan hydrolase, dextrin hydrolase, and amylase.

Japanese Kokai Publication Hei-3-193 describes that a slime can be removed effectively by using β-glucanase in combination with protease and amylase to disrupt the surface layer of a slime.

Japanese Kokai Publication Hei-4-91288 proposes the use of a β-glycosidase.

In using such an enzymatic agents, appearance of resistant strains and hazards, which are the drawbacks of antimicrobial agents, need not be considered. However, the representative enzyme levan hydrolase and the above-mentioned binary biocidal substance, β-glucanase and the like are useful for bacterial slimes but not effective enough for mold slimes, due to their specificity.

Other commercial β-glucosidase are not effective enough when used alone and must be used in combination with other kinds of enzymes. Moreover, they are expensive, difficult to formulate, and therefore, not suited for exploitation on an industrial scale.

SUMMARY OF THE INVENTION

In view of the above state of the art and for the purpose of screening out microorganisms capable of producing enzymes effective for Eumycetes slimes originating in molds, yeasts and the like, the inventors of the present invention screened a variety of microorganisms from soil and the like and, as a consequence, discovered a novel slime-decomposing enzyme producing strain of microorganism capable of producing an enzyme which can decompose slimes originating in various molds, yeasts and the like with a broad specificity. The present invention has been developed on the basis of the above finding.

The essence of the present invention resides in the very slime-decomposing enzyme producing strain of microorganism which belongs to the genus Cellulomonas and is capable of producing an enzyme effective for decomposition of a slime. The present invention is further directed to a process for producing a slime-decomposing enzyme using said slime-decomposing enzyme producing strain of microorganism and a method for slime control using said slime-decomposing enzyme.

DETAILED DESCRIPTION OF THE INVENTION

The present invention is now described in detail.

The slime-decomposing enzyme producing strain of microorganism of the present invention, which belongs to the genus Cellulomonas and has the property to be able to produce an enzyme effective for decomposing slimes, can be isolated by screening microorganisms isolated from soil sample for strains having activity to decompose slimes from paper-mill. As examples of such slime-decomposing enzyme producing microorganisms, there can be mentioned Cellulomonas SCI-H1 and Cellulomonas SCI-H2. These Cellulomonas SCI-H1 and Cellulomonas SCI-H2 strains are novel Cellulomonas bacteria which have not been described in the literature before, but have been discovered for the first time by the inventors of the present invention.

The method for isolating Cellulomonas SCI-H1 and SCI-H2 is first described.

Method for Isolation of Cellulomonas SCI-H1 and Cellulomonas SCI-H2

1. Primary screening

Using microorganisms isolated from soil or other samples, strains having activity to decompose slimes from paper-mill are screened out. The slimes for use in this screening are not reacted on by levan hydrolase.

For the assessment of slime-decomposing enzyme activity, for example, a piece (5 mm square) of flexible urethane foam is put in a test tube containing 5 ml of a white water medium containing 0.1 weight % of glucose, 0.05 weight % of starch, 0.1 weight % of peptone, and 0.05 weight % of yeast extract and adjusted to pH 6.0 and, after sterilization, the medium is inoculated with the slime. The inoculated medium is incubated at 30° C. under shaking for 4 days to allow a deposit of slime to form on the foamed urethane piece. (This slime formed on the urethane piece is hereinafter referred to as "urethane slime"). One piece of urethane slime is put in 5 ml of a medium adjusted to pH 7.0, composed of 1.0 weight % of peptone and 0.1 weight % of dipotassium hydrogen phosphate, and after sterilization, the medium is inoculated with the test strain and incubated at 30° C. for 3 days. The decrease in the urethane slime and the release of the slime from the urethane piece were visually assessed to estimate the slime decomposing activity and a useful strain is selected.

2. Secondary screening

To obtain a strain with a broad slime decomposing specificity, the paper-mill slimes resistant to levan hydrolase were used to form urethane slimes and strains with a broad specificity, i.e. activity to decompose many of the slimes, were selected. In this manner, Cellulomonas SCI-H1 and Cellulomonas SCI-H2 can be screened.

The taxonomical characteristics of Cellulomonas SCI-H1 and Cellulomonas SCI-H2 strains are described below in detail.

Taxonomical characteristics

The morphological, physiological, and chemotaxonomical characteristics of Cellulomonas SCI-H1 and SCI-H2 strains are presented in Tables 1 and 2. Cell component analysis was carried out with the cells grown in a Soybean-casein digest (SCD) liquid medium (Nippon Seiyaku Co.) under shaking (230 rpm) at 33° C. for 20 hours and harvested by centrifuging the culture broth.

TABLE 1

| | Taxonomical items | SCI-H1 | SCI-H2 |
|---|---|---|---|
| Morphology | Colonial morphology | Yellow, circular | Cream-colored, sinuate margin |
| | Cellular morphology | Rod bacteria Young culture Irregular rods, filamentous. Old culture Coccoid cells, giving V formations, irregular size | Rod bacteria Young culture Irregular rods, filamentous. Old culture Clavate, giving V formations, irregular size |
| | Motivity | − | − |
| | Sporogenesis | − | − |
| Physiology | Gram stain | + | + |
| | Aerobic culture | + | + |
| | Anaerobic culture | + | + |
| | Catalase | + | + |
| | Urease | + | − |
| | Temperature for growth | 20 to 40° C. | 20 to 40° C. |
| | pH for growth | pH 6 to 9 | pH 6 to 9 |
| Chemotaxonomy | G + C (mole %) | 73.7 | 73.8 |
| | Amino acid analysis of peptidoglycan (molar ratio) | Asp 1 Ser 1 Glu 1 Ala 2 Lys 1 | Asp 1 Ser 1 Glu 1 Ala 2 Lys 1 |
| | Peptide glycan | Group A | Group A |
| | Diamino acid | Lys | Lys |
| | Menaquinone | MK-9 (H4) | MK-9 (H4) |

TABLE 2

| | Physiology | | | |
|---|---|---|---|---|
| Carbohydrate | SCI-H1 | | SCI-H2 | |
| assimilation spectrum | Acid production | Gas production | Acid production | Gas production |
| L-arabinose | + | − | + | − |
| D-xylose | + | − | + | − |
| D-glucose | + | − | + | − |
| D-mannose | + | − | + | − |
| D-fructose | + | − | + | − |
| D-galactose | + | − | + | − |
| Maltose | + | − | + | − |
| Sucrose | + | − | + | − |
| Lactose | − | − | − | − |
| Starch | + | − | + | − |
| Trehalose | + | − | + | − |
| D-sorbitol | − | − | − | − |

TABLE 2-continued

| | Physiology | | | |
|---|---|---|---|---|
| Carbohydrate | SCI-H1 | | SCI-H2 | |
| assimilation spectrum | Acid production | Gas production | Acid production | Gas production |
| D-mannitol | − | − | − | − |
| Inositol | − | − | − | − |
| Glycerol | + | − | + | − |

Since both Cellulomonas SCI-H1 and Cellulomonas SCI-H2 were found to be gram-positive, facultative anaerobic irregular rods, they could be classified into the group of facultative anaerobes according to Bergey's Manual of Systematic Bacteriology, Vol. 2, p. 1261, (1986), Section 15 Irregular, Nonsporing Gram-Positive Rods. Included in this group are bacteria of 9 genera, with the genus Oerskovia, actinomycetes, as homologous reference.

Furthermore, the above two strains are both catalase-positive, with a GC content of the DNA of 74 weight %, a peptidoglycan composition of Group A (L-Lys-D-Ser-D-Asp type), a diamino acid type of Lys, and a menaquinone of MK-9 (H4). Therefore, in light of the relevant description in Bergey's Manual of Systematic Bacteriology, they were considered to belong to the genus Cellulomonas or the genus Oerskovia, and be akin to *Cellulomonas cellulans*.

As described in the same literature, the genus Oerskovia comprises two species, namely *Oerskovia xanthineolytica* and *Oerskovia turbata*. However, according to Zentralblatt feur Bacteriologie, Microbiologie und Hygiene, Abt. 1, Originale C, Vol. 3, 401, 1982 and International Journal of Systematic Bacteriology, Vol. 33, 438, 1983, the genus Oerskovia is considered to be the equivalent of the genus Cellulomonas.

Therefore, despite the differences found in colonial morphology, cellular morphology in old cultures, and urease activity, their identical peptidoglycan composition suggested that above-mentioned two strains are strains of the genus Cellulomonas, which are akin to *Cellulomonas cellulans*. Since none of known bacteria of this kind have slime-decomposing enzyme producing activity, the above strains were both considered to be novel strains.

The above Cellulomonas SCI-H1 and Cellulomonas SCI-H2 have been deposited with National Institute for Bioscience and Human Technology, the Agency of Industrial Science and Technology under the accession numbers of FERM BP-5166 and FERM BP-5167, respectively. It should, however, be understood that the strain of microorganism according to the present invention is not limited to these strains but can be any slime-decomposing enzyme producing strain of microorganism of the genus Cellulomonas.

In accordance with the present invention, the slime-decomposing enzyme can be produced by culturing at least one strain of said Cellulomonas SCI-H1 and Cellulomonas SCI-H2, or a slime-decomposing enzyme producing strain of the genus Cellulomonas containing a mutant thereof, and preparing the slime-decomposing enzyme from the culture broth.

For the production of the slime-decomposing enzyme from culture broth using at least one strain of said Cellulomonas SCI-H1 and Cellulomonas SCI-H2, culture of the strain can be carried out in a medium containing sources of carbon and nitrogen and inorganic salt. The carbon source that can be employed is not particularly restricted but may for example be chitin-containing materials such as chitin flake, chitin powder, and chitin-containing fungal cells, etc. and even the very slime to be decomposed. The nitrogen source is not restricted, either, but those nitrogenous materials which are conventionally used, such as peptone, meat extract, casamino acids, yeast extract, urea, ammonium salts, nitrates, etc., can be used independently or in combination. Among them, use of yeast extract either alone or in combination with other nitrogenous materials is preferred. The inorganic salt is not restricted, either, but a variety of inorganic salts for routine use, such as salts of phosphorus, potassium, magnesium, manganese, iron, calcium, sodium, etc., can be employed.

The proportions of those nutrients in the medium can be 0.1 to 5.0 weight %, preferably 0.2 to 2.0 weight %, of the carbon source, 0.1 to 3.0 weight %, preferably 0.2 to 1.0 weight %, of the nitrogen source, and 0.01 to 3.0 weight %, preferably 0.05 to 1.5 weight %, of the inorganic salt.

Culture can be carried out under whichever of anaerobic and aerobic conditions but aerobic culture is preferred. Aerobic culture can be carried out typically by using a shake flask or by aerated agitation culture in a fermentor.

The conditions of culture are pH 6.0 to 9.5, preferably pH 7.0 to 9.0, incubation temperature of 18° to 45° C., preferably 25° to 40° C., more preferably 37° C., and incubation time of 18 to 100 hours, preferably 24 to 35 hours.

In accordance with the present invention, the slime-decomposing enzyme is prepared from the culture broth upon completion of culture of said slime-decomposing enzyme producing strain of microorganism. The slime-decomposing enzyme according to the present invention may be a purified enzyme from said culture broth, the very culture broth containing enzymes, microorganism cells, and metabolites, or a crude extract available from a filtrate or centrifugal supernatant of the culture broth.

The purification mentioned above can be carried out by the routine procedure well known for the purification of enzymes in general.

The slime-decomposing enzyme prepared by using at least one strain of Cellulomonas SCI-H1 and Cellulomonas SCI-H2 in the above manner has not only chitinase activity but also β-1,3-glucanase (laminarinase), mannase, protease and the like enzyme activities. The activities and proportions of the respective enzymes responsible for said enzyme activities in the slime-decomposing enzyme vary with different medium compositions, cultural conditions, and enzyme purification procedures employed and, therefore, cannot be defined in general terms. However, for example, the enzymatic activities per litter of a centrifugal supernatant of the culture broth obtained by shake culture of each strain in a medium adjusted to pH 7.5, containing 0.5 weight % of chitin powder, 0.3 weight % of yeast extract, and 0.1 weight % of potassium dihydrogen phosphate at 30° C. for 3 days are as indicated in Table 3.

TABLE 3

| Enzyme | Substrate | pH | Enzymatic activity (units) | |
|---|---|---|---|---|
| | | | SCI-H1 | SCI-H2 |
| Chitinase | Chitin | 5.5 | 400 | 340 |
| β-1,3-Glucanase | Laminarin | 6.0 | 750 | 750 |
| Mannase | Mannan | 6.0 | 1400 | 1600 |
| Protease | Casein | 7.0 | 12000 | 4700 |

In Table 3, one enzyme unit represents the amount of each enzyme which releases 1 μ mole equivalent of the degradation product from the substrate in one hour, namely the amount of the enzyme which releases amino sugars in the case of chitinase, reduced sugars in the case of β-1,3-glucosidase and mannase, and tyrosine equivalent in the case of protease.

Among the above-mentioned enzymatic activities, chitinase activity and β-1,3-glucanase activity work synergistically to decompose the cell wall of molds, while mannase activity acts effectively on the cell wall of yeasts and the like. Moreover, β-1,3-glucanase activity is effective for bacteria having extracellular β-1,3-glucans as well.

Since the above slime-decomposing enzyme has several enzymatic activities as mentioned above, it is capable of controlling not only mold slimes but also yeast and bacterial slimes.

In accordance with the present invention, slime control of industrial water and prevention of sludge bulking can be accomplished by using the above-prepared slime-decomposing enzyme either alone or optionally in combination with levan hydrolase such as EDC-1 available from San Nopco Co., and/or chemical agents. For example, the enzyme of the present invention can be used with advantage for control of slimes in cooling water, water at paper-making processes, sewage water, plant effluents, and other waste water. This method for slime control enables removing slime from the various separative membranes used in the treatment of sewage water or industrial waste water or in the food, papermaking, and pharmaceutical industries. Furthermore, since the slime-decomposing enzyme of the present invention is capable of decomposing molds and other cells, it can be broadly utilized for cleaning of garbage cages in a kitchen sink, bathtubs, laundering machines, bathrooms, clothings, etc. or prevention against putrefaction of stored lumbers, food stuffs, drugs, feedstuffs, etc.

For the control of slimes in industrial water or removing slimes from separative membranes using the slime-decomposing enzyme of the present invention, an effective amount of the enzyme is added to the industrial water to be treated. The effective amount mentioned above varies according to the type, temperature, pH, and degree of microbial contamination of industrial water, but generally not less than 100 units, in terms of chitinase activity, per milliliter of said enzyme solution, culture broth, or crude extract from the culture filtrate or supernatant is preferably added to the industrial water at a concentration of not less than 1 ppm.

For the prevention of sludge bulking using the slime-decomposing enzyme of the present invention, an effective amount of the enzyme is added to the sludge to be treated. The effective amount mentioned above varies according to the type, temperature, pH, and degree of microbial contamination of sludge, but generally not less than 100 units, in terms of chitinase activity, per milliliter of said enzyme solution, culture broth, or crude extract from the culture filtrate or supernatant is preferably added to the sludge at a concentration of not less than 1 ppm.

For the treatment of waste water with the slime-decomposing enzyme of the present invention, an effective amount of the slime-decomposing enzyme is added to the waste water to be treated, which includes sewage water, industrial waste water, or a mixture thereof. While the effective amount mentioned above varies according to the type, temperature, pH, and degree of contamination of the waste water, preferably not less than 100 units, in terms of chitinase activity, per milliliter of said enzyme solution, culture broth, or crude extract available from the culture filtrate or supernatant is generally added to the waster water at a concentration of not less than 1 ppm.

Use of the culture broth containing microorganism cells as the slime-decomposing enzyme is conducive to a long-term effect, because said two strains in the present invention can grow even at high pH levels, for example even if they are added to basic water, the strains can be proliferate.

The addition of the enzyme to utility water, a sludge, or waste water in each of the above mode of use can be carried out continuously or intermittently. Furthermore, it is possible to add said culture cells, purified enzyme or crude extract as previously immobilized by physical adsorption on a carrier, by inclusion in a cage-like or other host material, or by microencapsulation.

For slime control in paper-making precesses, such as stock preparation, web-formation, white water circuit, and white water treatment, the slime-decomposing enzyme of the present invention can be added to the stock preparation stage, white water circuit, and/or white water treatment stage, namely to the pulper, mixing box, refiner, machine chest, drop box, wire pit, seal pit, white water pit, save-all, etc.

Cleaning of the garbage cage in a kitchen sink, bathtub, laundering machine, bathroom, or clothes with the slime-decomposing enzyme according to the present invention can be carried out by applying a detergent composition containing an effective amount of the enzyme in the routine manner. The effective amount mentioned above is dependent on the type, temperature, pH, and degree of microbial contamination of the applied substance but can generally be 0.1 to 200 units, in terms of chitinase activity, per milliliter.

Preservation of stored lumbers, foodstuffs, pharmaceutical products, feedstuffs, etc. with the slime-decomposing enzyme according to the present invention can be carried out by various methods such as dipping in an enzyme solution or direct application by dusting, coating, or incorporation of an effective amount of the slime-decomposing enzyme.

BEST MODE OF CARRYING OUT THE INVENTION

The following examples are intended to describe the present invention in further detail and should by no means be construed as defining the scope of the invention.

Example 1 Isolation of Cellulomonas SCI-H1 and Cellulomonas SCI-H2 strains

1. Primary screening

From among 1043 strains of microorganisms isolated from soil samples, strains having activity to decompose paper-mill slimes were screened out. The slimes used for this screening were those which showed no release of fructose when treated with San Nopco's levan hydrolase EDC-1 and tested by the resorcinol method and the TTC (2,3,5-triphenyl-2H-tetrazolium chloride) method as described in Japanese Kokoku Publication Sho-53-39395.

Slime-decomposing enzyme activity assays were carried out as follows. A piece (5 mm square) of flexible urethane foam was put in a test tube containing 5 ml of a white water medium containing 0.1 weight % of glucose, 0.05 weight % of starch, 0.1 weight % of peptone, and 0.05 weight % of yeast extract and adjusted to pH 6.0 and, after sterilization, the medium was inoculated with the above-mentioned slime. The inoculated medium was incubated at 30° C. under shaking for 4 days to let a slime grow on the foamed urethane piece. Then, 5 ml of a medium was prepared by adding 1.0 weight % of peptone and 0.1 weight % of dipotassium hydrogen phosphate to one piece of the above urethane slime and adjusting to pH 7.0, and after sterilization, the medium was inoculated with the test strain and incubated at 30° C. for 3 days. Then, the decrease in urethane slime and release of the slime from the urethane foam were visually determined to estimate slime-decomposing enzyme activity. By this procedure, 36 active strains were screened out.

2. Secondary screening

To select strains having a broad slime decomposing activity spectrum from among the above 36 strains selected by the primary screening, urethane slimes were prepared by using 11 paper-mill slimes indifferent to levan hydrolase, and strains with broad specificity which decomposed 7 of the urethane slimes were picked out. As a result, Cellulomonas SCI-H1 and Cellulomonas SCI-H2 strains were finally selected.

Example 2 Preparation of slime-decomposing enzyme solutions

Each of SCI-H1 and SCI-H2 was shake-cultured in a medium containing 0.3 weight % of chitin powder, 0.3 weight % of yeast extract, and 0.1 weight % of potassium dihydrogen phosphate (100 ml, pH 7.5) at 30° C. for 2 days. The resulting culture broth was centrifuged and the supernatant was adjusted to pH 6.0 with hydrochloric acid and filtered through a bacterial filter (0.45 μm) to provide a slime-decomposing enzyme solution derived from either SCI-H1 or SCI-H2.

Example 3 Slime decomposing analysis

A piece (5 mm square) of flexible urethane foam was put in a test tube containing 5 ml of a white water medium containing 0.1 weight % of glucose, 0.05 weight % of starch, 0.1 weight % of peptone, and 0.05 weight % of yeast extract and adjusted to pH 6.0 and, after sterilization, the medium was inoculated with each of the slime samples taken from the white water at 3 to 5 locations within each of 5 paper mills. The inoculated medium was incubated at 30° C. under shaking for 4 days to let an urethane slime form. Then, one piece of the urethane slime was added to 3 ml of each of the enzyme solutions prepared in Example 2 and after 24 hours of gentle shaking at 30° C., the release of the slime from the urethane piece was visually assessed to test slime decomposition. Separately, 100 μl of the stock solution of EDC-1 (levan hydrolase, San Nopco) was added to 3 ml of the culture broth obtained in Example 2, and the resulting enzyme solution was similarly evaluated. As a control, 3 ml of a 30-fold dilution of EDC-1 was used. A positive slime-releasing activity was designated as + and a negative slime-releasing activity was designated as −. The results are presented in Table 4. In Table 4, A Co. through E Co. represent the paper mills and the numerals represent the sampling locations.

TABLE 4

| Slime | SCI-H1 | SCI-H2 | SCI-H1 + EDC-1 | SCI-H2 + EDC-1 | EDC-1 |
|---|---|---|---|---|---|
| A Co. -1 | + | + | + | + | − |
| -2 | + | + | + | + | − |
| -3 | + | + | + | + | − |
| -4 | + | + | + | + | + |
| -5 | − | − | + | − | − |
| B Co. -1 | − | − | − | + | + |
| -2 | + | + | + | + | − |
| -3 | − | − | + | + | + |
| C Co. -1 | − | − | + | + | + |
| -2 | − | + | − | + | + |
| -3 | − | − | − | − | − |
| D Co. -1 | + | + | + | − | − |
| -2 | + | + | + | + | − |
| -3 | + | − | + | + | + |
| -4 | − | − | + | + | + |

TABLE 4-continued

| Slime | | SCI-H1 | SCI-H2 | SCI-H1 + EDC-1 | SCI-H2 + EDC-1 | EDC-1 |
|---|---|---|---|---|---|---|
| E Co. | -1 | − | − | + | − | + |
| | -2 | − | − | − | − | − |
| | -3 | + | + | + | + | − |
| | -4 | + | − | + | + | + |
| | -5 | − | + | + | + | + |

It is apparent from Table 4 that each of the enzyme solutions prepared from cultures of the strains of the present invention decomposed various EDC-1-resistant slimes much effectively and that when they were used in combination with EDC-1, a still broader variety of slimes could be decomposed.

Example 4 Prevention test of formation of slimes

Enzyme solutions were prepared by the same procedure as described in Example 2. One piece (5 mm square) of urethane foam was put in a medium prepared by adding 0.2 weight % of glucose, 0.1 weight % of starch, 0.2 weight % of peptone, and 0.1 weight % of yeast extract to 2 ml of white water and adjusted to pH 6.0 and, after sterilization, the medium was inoculated with one pincer equivalent of the slime from each of A Co. −1, B Co. −2, D Co. −1, and E Co. −3 shown in Table 4. Then, 2 ml of the enzyme solution obtained in Example 2, either as it was or after 10 minutes of heat treatment at 100° C., was added and the mixture was incubated at 30° C. under shaking for 7 days to examine the formation of a slime on the urethane piece. The slimes used were those which proved to resist hydrolysis by EDC-1 in Example 2. A positive slime formation was designated as +, a partial slime formation as ± and a negative slime formation as −. The results are presented in Table 5.

TABLE 5

| | SCI-H1 | | SCI-H2 | |
|---|---|---|---|---|
| Slime | Untreated | Heat-treated | Untreated | Heat-treated |
| A Co. -1 | − | + | − | + |
| B Co. -2 | + | + | − | + |
| D Co. -1 | − | + | + | + |
| E Co. -3 | − | + | ± | + |

It is apparent from Table 5 that whereas a positive slime formation was found when the heat-deactivated enzyme solution was added, no slime formation was noted when the untreated enzyme solution was added and that, therefore, the enzyme solutions obtained by the method of the invention are effective in preventing formation of slimes.

Example 5 Cytolysis test

Using 12 strains, namely molds a to 1, as isolated from white water slimes and 12 strains of molds from commercial sources, the cytolytic effects of the enzymes were evaluated. Czapek medium (5 ml) containing one piece (5 mm square) of urethane foam was inoculated with a loopful of each molds and the inoculated medium was incubated at 28° C. for 4 days to let the mold cells grow on the urethane piece. This mold cells was washed with saline and 3 ml of each enzyme solution from SCI-H1 and SCI-H2 as prepared in Example 2 was added. The mixture was reacted at 30° C. under shaking for 2 days and the release of the mold cells from the urethane piece was evaluated. As control, 3 ml of a 30-fold dilution of EDC-1 was used. Complete release of mold cells from the urethane piece was designated as ++, partial release as +, and no release as −. The results are presented in Table 6. In the table, a to 1 represent molds isolated from white water slimes.

TABLE 6

| Fungal strains (isolated and commercial strains) | SCI-H1 | SCI-H2 | EDC-1 |
|---|---|---|---|
| Isolated strain a | ++ | ++ | − |
| Isolated strain b | ++ | ++ | − |
| Isolated strain c | ++ | ++ | − |
| Isolated strain d | ++ | ++ | − |
| Isolated strain e | ++ | ++ | − |
| Isolated strain f | ++ | ++ | − |
| Isolated strain g | ++ | ++ | − |
| Isolated strain h | ++ | ++ | − |
| Isolated strain i | ++ | ++ | − |
| Isolated strain j | ++ | ++ | − |
| Isolated strain k | + | ++ | − |
| Isolated strain 1 | ++ | ++ | − |
| *Aspergillus usutus* IFO 4104 | ++ | + | − |
| *Aspergillus oryzae* IFO 4075 | + | ++ | − |
| *Aspergillus fumigatus* IFO 4057 | ++ | ++ | − |
| *Penicillium oxalicum* IFO 5748 | ++ | ++ | − |
| *Penicillium urticae* IFO 7010 | + | ++ | − |
| *Penicillium citrinum* IFO 4631 | ++ | ++ | − |
| *Trichoderma longibrachiatum* IFO 4847 | + | ++ | − |
| *Aureobasidiumn pullulans* IFO 4464 | ++ | ++ | − |
| *Fusarium solani* IFO 5891 | ++ | ++ | − |
| *Geotricum candidum* IFO 4597 | ++ | ++ | − |
| *Mucor flagillis* IFO 6449 | − | − | − |
| *Rhizopus javanicus* IFO 5441 | − | − | − |

It is apparent from Table 6 that the enzyme solutions obtained by the method of the present invention act on the cellular structures of various molds, to release the cells and are effective particularly for control of mold slimes.

INDUSTRIAL APPLICABILITY

The enzyme solution obtainable by the process of the present invention display excellent effects in the decomposition and prevention of mold slimes particularly, and can be applied with advantage to control of slimes in industrial water such as white water in papermaking processes or cooling water, removing slime from separative membranes, prevention of sludge bulking, cleaning of garbage cages in a kitchen sink etc., and preservation of lumbers, among other applications.

I claim:

1. A slime-decomposing enzyme producing strain of microorganism characterized by belonging to the genus Cellulomonas and capable of producing an enzyme for decomposition of slimes.

2. The slime-decomposing enzyme producing strain of microorganism according to claim 1, which is Cellulomonas SCI-H1.

3. The slime-decomposing enzyme producing strain of microorganism according to claim 1, which is Cellulomonas SCI-H2.

4. A process for producing a slime-decomposing enzyme characterized by culturing a slime-decomposing enzyme producing strain of microorganism belonging to the genus Cellulomonas and capable of producing an enzyme effective for decomposition of slimes and preparing the slime-decomposing enzyme from the resulting culture broth.

5. The process for producing a slime-decomposing enzyme according to claim 4 wherein said slime-decomposing enzyme-producing strain of microorganisms is at least one kind of Cellulomonas SCI-H1 and Cellulomonas SCI-H2.

6. A method for controlling slimes in industrial water characterized in that an effective amount of the slime-decomposing enzyme prepared by the process for producing a slime-decomposing enzyme according to claim 4 is added to the industrial water.

7. A method of controlling paper-mill slimes characterized in that an effective amount of the slime-decomposing enzyme prepared by the process for producing a slime-decomposing enzyme according to claim 4 is added to at least one of the stock preparation process, white water circuit, and white water treatment process in paper mill processes.

8. A method of preventing sludge bulking characterized in that an effective amount of the slime-decomposing enzyme prepared by the process for producing a slime-decomposing enzyme according to claim 4 is added to a sludge.

9. A method for waste water treatment characterized in that an effective amount of the slime-decomposing enzyme prepared by the process for producing a slime-decomposing enzyme according to claim 4 is added to waste water.

10. A method of cleaning a garbage cage in a kitchen sink, a bathtub, a laundering machine, a bathroom, or clothes characterized in that an effective amount of the slime-decomposing enzyme prepared by the process for producing a slime-decomposing enzyme according to claim 4 is applied to the garbage cage in a kitchen sink, bathtub, laundering machine, bathroom, or clothes.

11. A method of preserving a stored lumber, a foodstuff, a pharmaceutical product, or a feedstuff characterized in that an effective amount of the slime-decomposing enzyme prepared by the process for producing a slime-decomposing enzyme according to claim 4 is applied to the stored lumber, foodstuff, pharmaceutical product, or feedstuff.

12. A method for controlling slimes in industrial water characterized in that an effective amount of the slime-decomposing enzyme prepared by the process for producing a slime-decomposing enzyme according to claim 5 is added to the industrial water.

13. A method of controlling paper-mill slimes characterized in that an effective amount of the slime-decomposing enzyme prepared by the process for producing a slime-decomposing enzyme according to claim 5 is added to at least one of the stock preparation process, white water circuit, and white water treatment process in paper mill processes.

14. A method of preventing sludge bulking characterized in that an effective amount of the slime-decomposing enzyme prepared by the process for producing a slime-decomposing enzyme according to claim 5 is added to a sludge.

15. A method for waste water treatment characterized in that an effective amount of the slime-decomposing enzyme prepared by the process for producing a slime-decomposing enzyme according to claim 5 is added to waste water.

16. A method of cleaning a garbage cage in a kitchen sink, a bathtub, a laundering machine, a bathroom, or clothes characterized in that an effective amount of the slime-decomposing enzyme prepared by the process for producing a slime-decomposing enzyme according to claim 5 is applied to the garbage cage in a kitchen sink, bathtub, laundering machine, bathroom, or clothes.

17. A method of preserving a stored lumber, a foodstuff, a pharmaceutical product, or a feedstuff characterized in that an effective amount of the slime-decomposing enzyme prepared by the process for producing a slime-decomposing enzyme according to claim 5 is applied to the stored lumber, foodstuff, pharmaceutical product, or feedstuff.

* * * * *